US006125845A

United States Patent [19]

Halvorsen et al.

[11] Patent Number: 6,125,845

[45] Date of Patent: Oct. 3, 2000

[54] RESPIRATOR FIT-TESTING WITH SIZE SELECTED AEROSOL

[75] Inventors: Thomas G. Halvorsen, Blaine; Patricia B. Keady McDonald, Lino Lakes, both of Minn.

[73] Assignee: TSI Incorporated, St. Paul, Minn.

[21] Appl. No.: 08/939,995

[22] Filed: Aug. 29, 1997

[51] Int. Cl.[7] .................................................... A61M 15/00

[52] U.S. Cl. ................................ 128/200.24; 128/202.22; 128/205.29

[58] Field of Search ......................... 128/200.24, 202.22, 128/200.14, 205.27, 205.29

[56] References Cited

U.S. PATENT DOCUMENTS

| | | | |
|---|---|---|---|
| Re. 31,952 | 7/1985 | Wilcox et al. | 73/40.7 |
| 3,806,248 | 4/1974 | Sinclair | 356/37 |
| 4,055,075 | 10/1977 | Allan et al. | 73/40.7 |
| 4,324,568 | 4/1982 | Wilcox et al. | 55/97 |
| 4,402,214 | 9/1983 | Morgan et al. | 73/40.7 |
| 4,494,403 | 1/1985 | Bowers et al. | 73/40.7 |
| 4,515,007 | 5/1985 | Herman | 73/38 |
| 4,914,957 | 4/1990 | Dougherty | 73/40 |
| 5,117,190 | 5/1992 | Pourprix | 324/452 |
| 5,299,448 | 4/1994 | Maryyanek et al. | 73/40 |
| 5,428,220 | 6/1995 | Ehara | 250/281 |
| 5,596,136 | 1/1997 | Flagan et al. | 73/28.04 |
| 5,606,112 | 2/1997 | Flagan et al. | 73/28.04 |

FOREIGN PATENT DOCUMENTS 1422188 1/1976 United Kingdom .

OTHER PUBLICATIONS

"Quantitative Fit Testing Techniques and Regulations for Tight Fitting Respirators: Current Methods Measuring Aerosol or Air Leakage, and New Developments", Hee Han, et al., *American Industry Hygiene Association Journal* 58:219–228 (1997).

"Fit Test for Filtering Facepieces: Search for a Low Cost Quantitative Method", Myojo, et al., *Am. Ind. Hyg. Assoc. Journal* (55(9): 797–805 (1994).

(List continued on next page.)

*Primary Examiner*—Aaron J. Lewis
*Attorney, Agent, or Firm*—Frederick W. Niebuhr

[57] ABSTRACT

A system and process for respirator fit-testing are disclosed. The system includes conduits for taking first and second aerosol samples, from inside of the respirator mask and from outside of the mask, respectively. The samples are provided to a radial differential mobility analyzer for generating first and second modified samples corresponding to the aerosol samples. The modified samples are provided to a condensation particle counter, which generates first and second concentration values representing concentrations of suspended elements in the respective modified samples. Comparison of the concentration values yields a fit factor indicating how effectively the respirator seals against leaks. Alternative embodiment systems employ a cylindrical DMA, an electrical precipitator, or an inertial separating device in lieu of the radial DMA. For generating concentration values, an electrometer, a photometer or an optical particle counter can be used in lieu of the condensation particle counter. The system facilitates testing in ambient conditions reducing costs and enabling closer simulation of actual working conditions.

40 Claims, 6 Drawing Sheets

OTHER PUBLICATIONS

"Aerosol Penetration through Filtering Facepieces and Respirator Cartridges", Chen, et al., *Am. Ind. Hyg. Assoc. Journal* 53(9): 566–574 (1992).

"Validation of a Quantitative Fir Test for Dust/Fume/Mist Respirators: Part I", Iverson, et al., *Appl Occup. Environ. Hyg.* 7(3) Mar. 1992.

"New Methods for Quantitative Respirator Fit Testing with Aerosols", Willeke, et al., *Am. Ind. Hyg. Assoc. Journal*, pp. 121–125, Feb. 1981.

"Radial Differential Mobility Analyzer", Zhang, et al., *Aerosol Science and Technology*, 23: 357–372 (1995).

"A Quantitative Fit Test for Dust/Mist Respirators: Part II", Danisch, et al., *Appl Occup. Environ. Hyg.*, 7(4) p. 241–245, Apr. 1992.

"Numerical Modeling of the Performance of the Differential Mobility Analyzer for Nanometer Aerosol Measurements", Chen, et al., *J. Aerosol Sci.*, vol. 26, Suppl 1. Pp. S141–S142, 1995.

RESPIRATOR FIT-TESTING WITH SIZE SELECTED AEROSOL

BACKGROUND OF THE INVENTION

The present invention relates to instruments and processes for evaluating filtration devices as to leakage, more particularly for the quantitative fit-testing of respirators by measuring concentrations of particles or other suspended elements, inside and outside of a respirator mask.

There are certain occupations, e.g. firefighting, mining, construction, manufacturing and refining, that involve at least occasional exposure to airborne contaminants that can range from mildly irritating to toxic. Respirators are recommended and frequently are required under regulations of the Occupational Safety and Health Administration (OSHA).

Some respirators reply on a tight-fitting face seal to protect the wearer. This invention is directed at testing that seal. The National Institute for Occupational Safety and Health (NIOSH) has classified particulate air-purifying respirators according to 42 CFR Part 84. Three major classes exist within this new standard: class 95, 99 and 100. This invention, however, is directed to air-purifying respirators that rely on the surrounding environment as a source of breathing air. These respirators, designed to remove contaminants from the ambient air, are smaller, easier to maintain and less restrictive in the sense of allowing more freedom of movement. The National Institute for Occupational Safety and Health (NIOSH) has classified particulate air-purifying respirators into four groups: single-use; dusts and mists (DM); dusts, mists and frames (DMF); and high-efficiency particulate air (HEPA) filters.

While the effectiveness of a respirator depends in part on the efficiency of the filter or filters involved, the respirator fit also is of paramount concern. A poorly fitting respirator allows contaminants to flow into the breathing compartment formed by the mask, usually as a wearer inhales. Leakage occurs primarily along the interface of the mask with the face of the wearer, where a properly fitting mask forms a tight seal. A variety of factors can contribute to a poor respirator fit, including selection of a mask of incorrect size or shape, a fault along the edge of the mask intended to form the seal, improper technique in wearing the mask, and facial hair. A poorly fitting respirator mask can lead to considerable exposure to contaminants.

Accordingly, various regulatory agencies have established requirements for the fit-testing of respirators, and standards for determining whether a given respirator fit provides an acceptable seal against leakage.

There are several known approaches to respirator fit-testing. One, known as qualitative fit-testing, relies on the subjective response of an individual wearing the respirator upon exposure to an odor-producing aerosol, such as smoke or a suspension of liquid droplets, e.g. banana oil. Quantitative fit-testing is considered more accurate and more reliable. A common method of quantitative fit-testing involves taking particle concentration measurements, both inside of a respirator mask and just outside of the mask. This is accomplished by using a vacuum pump to draw an aerosol sample from the atmosphere just outside the mask, and then drawing another aerosol sample from within the mask, either by using a sampling adapter or a test mask with a face piece modified to receive a sampling tube. The two samples are provided, alternatively, to a condensation particle counter (also known as a condensation nucleus counter) that generates particle counts indicating the respective concentrations of the tested aerosol samples.

The two counts are compared by providing a ratio of the count outside the mask to the count inside the mask, known as the "fit factor". A higher fit factor indicates a filtration that effectively seals against leakage.

The validity of this test is based largely on an assumption that the count or concentration inside the mask is due to leakage rather than penetration through the filter, i.e. an assumption that the filter is nearly 100 percent efficient.

The accuracy of this assumption depends upon the type of filter involved, and the size of the particles or other suspended elements. Both high efficiency filters and low efficiency filters have efficiencies that vary with particle size. More particularly, each filter has a minimum efficiency (corresponding to a maximum particle penetration rate) at a midpoint along a particle size spectrum. Efficiency rises (reflecting reduced penetration) in both directions from the midpoint. Typically the midpoint occurs within a particle size range of 0.1 to 0.3 microns.

HEPA filters are at least 99.97 percent efficient, even at the minimum-efficiency midpoint. Other filters are considerably less efficient. For example, FIG. 1 shows on a log/log scale a fractional filtration efficiency curve representative of lower efficiency filters. The curve shows a minimum efficiency slightly over 92 percent at a particle size slightly less than 0.2 microns. For particles exceeding 0.5 microns or less than about 0.045 microns, the efficiency exceeds 99.9 percent.

While actual curves and values will vary depending on the filter class and the brand of filter within a given class, it is clear that when a class 95 respirator is exposed to a polydisperse aerosol over the size spectrum illustrated in FIG. 1, a relatively large number of particles at and near the most penetrating size pass through the filter and are detected inside the respirator mask. In practice, the number of particles entering the mask through the filter is substantially larger than the number entering the mask due to face-seal leakage. The result is a severe distortion of the calculated fit factor, erroneously indicating a poor fit when the respirator in fact may fit properly. As a result, class 99 or class 100 filters are either recommended or required for respirator fit-testing, even when the respirators involved are intended for use with class 95 or other less efficient filters.

Those of skill in the art are aware of this problem, and increasingly concerned because lower efficiency filters have gained acceptance for a wider range of uses. A related concern is exemplified by a class of respirators known as "N95" filtering facepieces. In their most common configuration, these respirators consist of a mask composed entirely of the filter medium, without a supporting elastomeric mask. The N95 respirator is greater than 95 percent efficient at the most penetrating particle size. These respirators have penetration sufficient to overwhelm the particles coming through leaks, leading to inaccurate results if the fit-testing is conducted in a polydisperse aerosol environment. Recent regulatory changes have resulted in an upsurge of N95 respirator production and usage, and government regulations continue to require fit-testing.

In view of these difficulties, researchers in this area have tried several approaches to fittesting respirators without HEPA filters. One approach involves generating a suitable monodisperse aerosol, e.g. with all particles at or about 2.5 micrometers in diameter. Dust/mist filters, N95 filters, and other low efficiency filters are considerably more efficient with respect to particles at or near 2.5 microns in diameter. Results based on this type of testing, however, are reliable only if testing occurs within a controlled atmosphere including only the monodisperse aerosol. Maintaining this atmosphere is expensive, requiring an aerosol generator to produce the monodisperse aerosol and a chamber or other enclosure surrounding the person wearing the respirator under test. The enclosure limits the individual's ability to perform certain exercises or movements during fit-testing. This technique is described in an article entitled "Validation of a Quantitative Fit-Test for Dust/Fume/Mist Respirators: Part I", Iverson et al; *Applied Occupational Environmental Hygiene*, March 1992, pp. 161–167.

Another approach is based on the discovery that for DM and DFM respirators, the relationship between filter penetration and leakage depends upon the face velocity (flow rate). The approach is described in an article entitled "Fit-Testing for Filtering Face Pieces: Search for a Low-Cost, Quantitative Method", Myojo et al; *American Industrial Hygiene Association Journal,* 55 (9), 1994, pp. 797–805. Tests were conducted on mannequins and human subjects, both breath-holding and normal breathing. The technique, however, is limited primarily to aerosols in the submicrometer size range. Also, the reliability of tests on human subjects breathing normally depends on the ability to predict and monitor the subject's inhalation rate.

Another known fit-test involves using an optical particle counter in combination with lower efficiency filters, such as dust/mist and N95. The complete polydisperse aerosol is sampled. Due to the limited capacity of the optical particle counter, i.e. its ability to detect only relatively large particles (more than 0.5 microns in diameter), the tendency of penetrating particles to bias leakage test results is reduced. However, the relatively small number of large particles occurring naturally in ambient conditions limits the utility of this approach, because the number of sensed particles is not sufficient to afford statistical accuracy.

Therefore, it is an object of the present invention to provide a process for testing filtration devices for leakage, in which reliable results can be obtained based on aerosol sampling in ambient, naturally occurring conditions.

Another object is to provide a system for leak-testing filtration devices, that does not requires either a device for generating a prescribed artificial atmosphere or an enclosure for keeping an individual within an artificial atmosphere during testing, although it may advantageously employ a polydisperse aerosol generator in certain cases.

A further object is to provide a respirator fit-testing system that allows more freedom of movement for the individual during testing, to facilitate duplication of on-the-job tasks and movements.

Yet another object is to provide a respirator fit-testing process based on sampling polydisperse aerosols under ambient conditions, then selecting a predetermined range of particle sizes within the sampled aerosols to improve statistical accuracy and avoid biasing of leak-test results due to particle penetration.

SUMMARY OF THE INVENTION

To achieve these and other objects, there is provided a process for testing a filtration device for leakage, including:

a. using a filtration device with a filter to form an enclosure within a polydisperse aerosol that includes a polydisperse suspension of elements in a gaseous medium;

b. collecting a first aerosol sample of the aerosol from the atmosphere outside of the enclosure;

c. collecting a second aerosol sample of the polydisperse aerosol from inside of the enclosure;

d. segregating the elements of the first and second aerosol samples according to a predetermined element characteristic, thereby to retain within each aerosol sample only selected elements that exceed a fractional filtration efficiency threshold with respect to the filter, to provide first and second modified samples corresponding respectively to the first and second aerosol samples; and e. generating first and second concentration values representing concentrations of the selected elements in the first modified sample and in the second modified sample, respectively.

The first and second concentration values can be compared to determine a degree of leakage of the aerosol into the enclosure. Typically this is done by generating a fit factor, i.e. a ratio of the first concentration value (outside) to the second concentration value (inside). A higher fit factor indicates a filtration device that more effectively seals against leakage.

The preferred element characteristic for segregating the elements is size. For example, all suspended elements less than a predetermined threshold diameter are retained within the modified samples, while the larger particles are removed. A frequently preferred alternative is to retain the suspended elements falling within a predetermined size range, to exclude not only particles larger than a first size, but also particles smaller than a second, smaller size.

A highly preferred approach is to separate the suspended elements, based on their electrical mobility. Several instruments are available for this purpose. For example, a differential mobility analyzer (DMA) is particularly well suited for separating particles within a predetermined range of sizes. An electrical precipitator is advantageously employed to select all particles having diameters less than a predetermined threshold.

As an alternative, inertial separators can separate particles based on "aerodynamic diameter," i.e., particle mass and shape, rather than electrical mobility. Suitable devices include impactors, virtual impactors, cyclones, horizontal elutriators and centrifugal separators. These devices separate particles based on their aerodynamic diameters.

Similarly, a variety of instruments are suitable for generating the concentration values ultimately compared to determine leakage. Condensation particle counters (also known as condensation nucleus counters) are particularly well suited for measuring fine particles, with diameters less than about 0.1 micrometers. For large particles, e.g. 0.5 micrometer or greater diameters, optical particle counters and photometers are useful alternatives.

The process is particularly well suited for the fit-testing of respirators having filters in the lower efficiency range, e.g. in the 95 and N95 classes. These filters, vulnerable to high penetration rates at certain sizes (e.g. 0.2 microns), are highly efficient with respect to particles substantially larger and substantially smaller in size. Using the process and system of the present invention, elements not within a predetermined size range are physically separated from the sampled polydisperse aerosols, to provide the modified aerosols from which concentrations are determined. There is no need for an aerosol generator, and no need for a chamber to enclose a specially generated atmosphere. Individuals are able to breathe normally while testing the respirators, and can perform physical tasks and exercises that are expected to arise in the real working environment. Selection of appropriate size ranges ensures that element concentrations within respirators reflect leakage rather than filter penetration, and encompass a sufficient number of elements to ensure statistical accuracy. Test results are more reliable because test conditions—with no artificial atmosphere, no undue confinement of the individual, no exchange of filter types, and no subjective response required to qualitative fit testing—more closely reflect actual workplace conditions.

IN THE DRAWINGS

For a further understanding of the above and further advantages, reference is made to the following detailed description and to the drawings, in which.

DETAILED DESCRIPTION OF THE PREFERRED EMBODIMENTS

Figure 1:
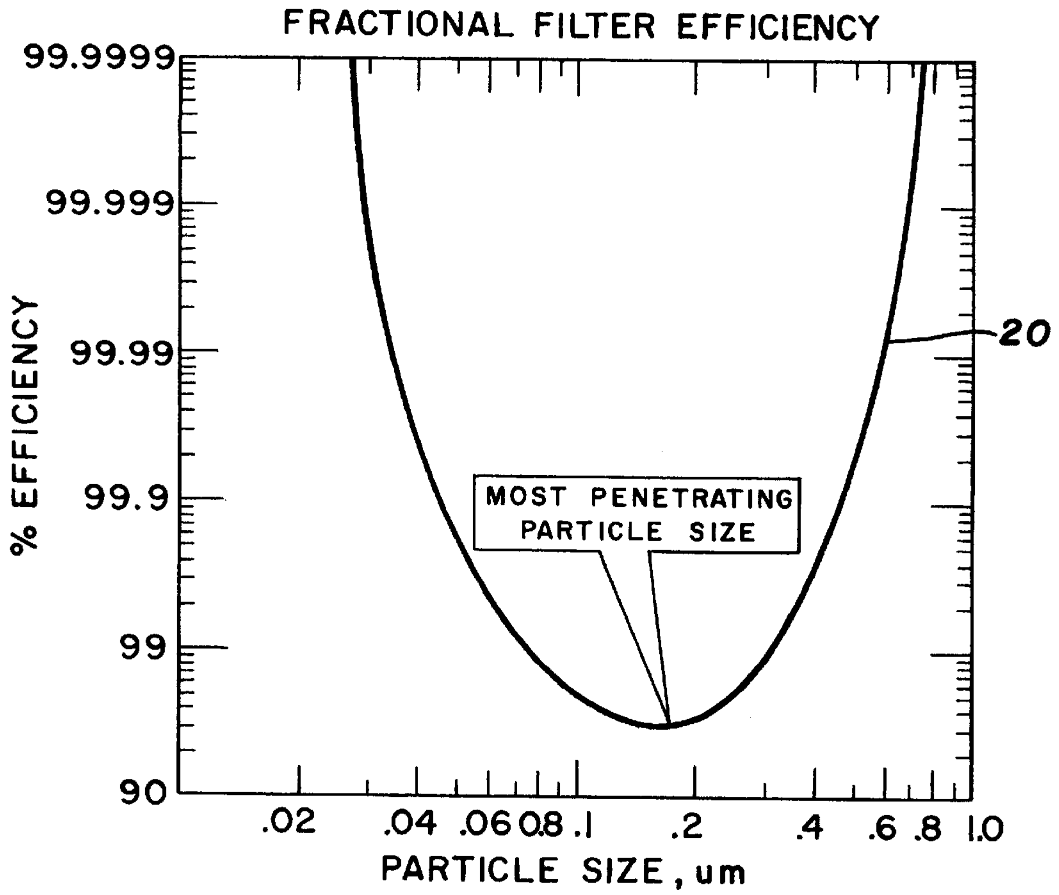
FIG. 1 is a plot of fractional filter efficiency versus particle size, for a typical low efficiency filter.
Figure 2:
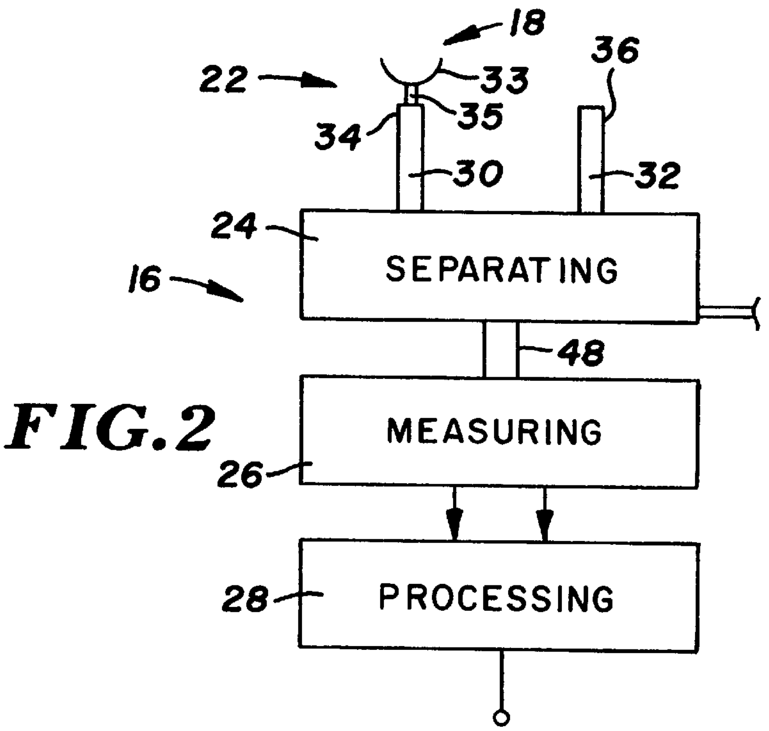
FIG. 2 is a schematic view of a respirator fit-testing system constructed in accordance with the present invention.

Turning now to the drawings, there is shown in FIG. 2 a testing system 16 for evaluating a filtration device for leakage, as opposed to particle penetration. In particular, system 16 is used to conduct quantitative fit-tests on filtration devices such as an air purifing respirator 18. Respirator 18 is from one of several respirator classes, e.g. N95, that exhibit a fractional filtration efficiency that varies with particle size. As indicated by a plot 20 on a log/log scale of efficiency/size (FIG. 1), these filters typically have a minimum efficiency (maximum particle penetration) at some midpoint on the size spectrum, typically 0.1 to 0.3 micrometers. Efficiency increases in either direction from the midpoint.

The variance in filtration efficiency can have a considerable impact on the fit-testing of respirator 18, particularly when polydispersed aerosols are employed. As used in this application, the term "aerosol" refers to a suspension of elements (e.g. solid particles or droplets) in a gaseous medium. Atmospheric or ambient air is an example of an aerosol, with air as the gaseous medium supporting typically 3,000–10,000 elements per cubic cm.

Ambient air further is a "polydisperse aerosol", because the particles or other elements vary widely in size across the range illustrated in FIG. 1. By contrast, a "monodisperse aerosol" is comprised of particles at or near a particular diameter.

System 16 is designed to overcome a problem encountered when respirator 18 is tested by sampling a polydisperse aerosol. The problem, discussed in more detail above, is the tendency of aerosol particles or other elements in the low efficiency mid-range to penetrate the respirator's filter, biasing test results toward an inaccurately low fit factor, i.e. indicating a greater degree of leakage than actually occurred.

Through system 16, the problem is overcome without the need to generate a monodisperse aerosol especially for testing, and without the need to confine the test subject within an artificial atmosphere. To this end, system 16 includes an aerosol sampling stage 22, an aerosol element separating stage 24, a concentration measuring stage 26 and a processing stage 28.

Sampling stage 22 includes a pair of sampling conduits 30 and 32, typically flexible tubing or hose constructed of a suitable polymer. Conduit 30 is adapted to draw an aerosol sample from inside of a respirator mask 33 to be tested. Typically, a test mask of the type to be used is equipped with a face-piece probe 35 to which an entrance port 34 is coupled. An entrance port 36 of conduit 32 is positioned proximate the mask but outside of it. Thus, conduit 32 draws an aerosol sample from the atmosphere or environment immediately surrounding the mask under test. In accordance with the present invention, the test is conducted either under ambient conditions, within a combination of an ambient and a supplemental aerosol, or within an environment which, to the extent practicable, duplicates the working conditions the individual is expected to encounter when wearing the respirator. No monodisperse aerosol is generated into the atmosphere about the mask, nor is the test conducted within a chamber or other enclosure for containing a specially generated atmosphere. Accordingly, the aerosol samples drawn into conduits 30 and 32 are virtually certain to be polydisperse.

The samples drawn into conduits 30 and 32 are provided to separating stage 24. Samples are not drawn until after a purge cycle of about fifteen seconds, during which the individual wearing the respirator breathes normally. At the separating stage, each of the aerosol samples is modified in view of the type of mask being tested. Some of the polydisperse suspended elements (usually particles) in the aerosol are selected according to their size or another suitable characteristic, to provide in each case a modified aerosol sample, in which the suspension consists of those particles for which the respirator filter involved is highly efficient. In other words, particles which have an unacceptably high penetration into the filter, typically due to their size, are excluded from the sample. The resulting modified sample can be either a monodisperse aerosol or a polydisperse aerosol. In either event, however, the remaining particulate has a sufficiently low penetration with respect to the filter under test, to justify an assumption that virtually all of such particles found in the respirator sample entered the mask due to leakage.

Figure 3:
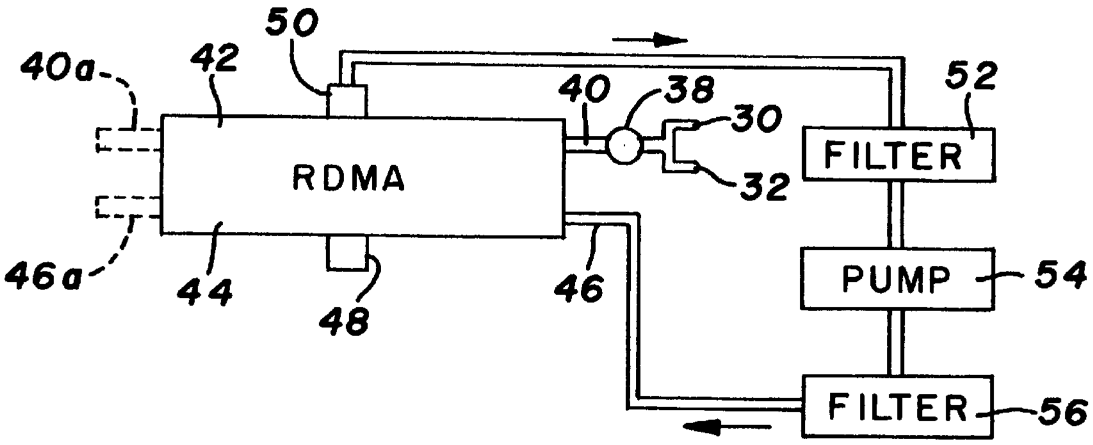
FIG. 3 is a schematic representation of a radial differential mobility analyzer and related components of a separator stage of the system.

FIG. 3 illustrates the separation stage in greater detail. The samples from conduits 30 and 32 are provided alternatively through a selector valve 38 to an inlet 40 of a radial differential mobility analyzer (radial DMA) 42. Radial DMA 42 has a disk-shaped housing 44 generally symmetrical about a central axis which is not illustrated but which would be vertical in FIG. 3. As indicated in broken lines at 40*a,* one or more additional inlets can be provided, circumferentially about DMA 42. In such cases, all of the inputs simultaneously receive either the mask sample or the ambient sample. The radial DMA utilizes a clean sheath air flow, provided to the DMA at an inlet 46 for eventual merger with the sample flow within the DMA. As is explained in more detail below, outputs from the DMA include a modified sample exit 48 and an excess air exit 50. The excess air flow is directed through a filter 52 to a diaphragm pump 54 that governs the sheath flow rate, through another filter 56 and then returned to the DMA through inlet 46. Additional sheath air inlets can be provided.

Figure 4:
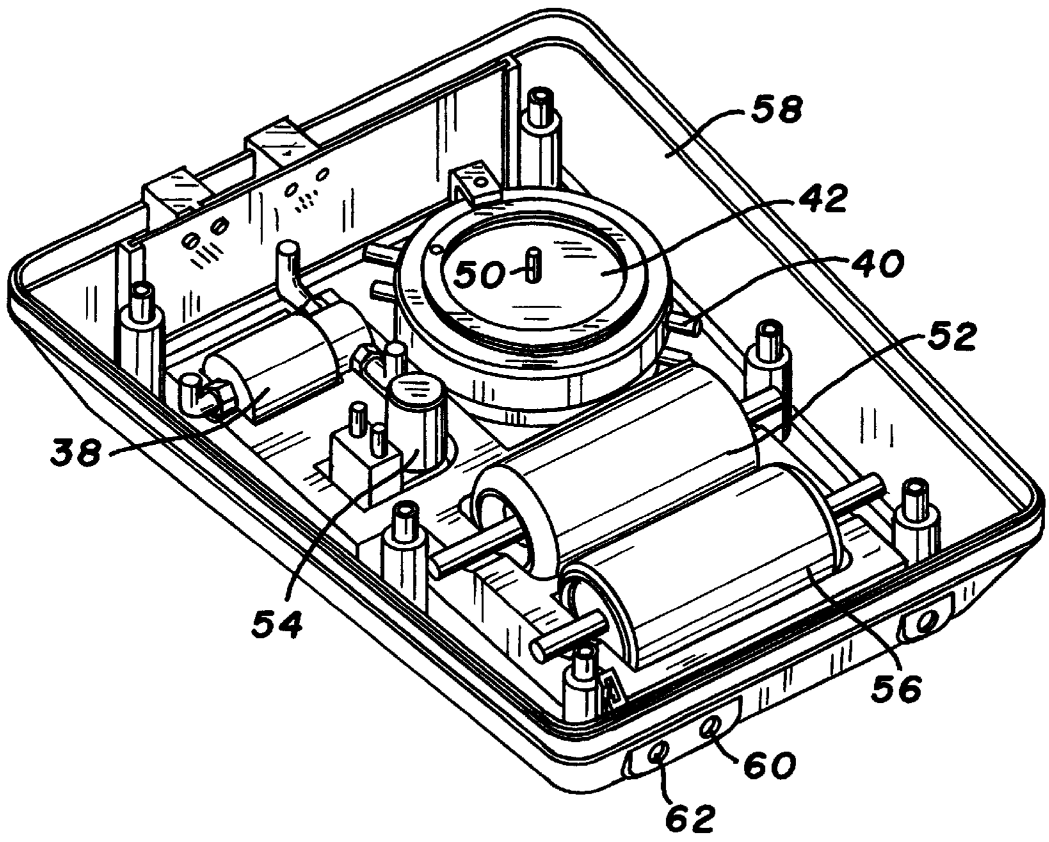
FIG. 4 is a perspective view of the radial DMA and related components.

FIG. 4 illustrates an advantage of using radial DMA 42 for aerosol separation; namely, that the DMA and its components can be packaged into a relatively small container 58 as shown, with filters 52 and 56 side by side. Pump 54 is situated between the filters and selector valve 38. Inlet ports 60 and 62 for the mask sample and ambient sample, respectively, are side by side and upstream of the valve. Flexible tubing couples the components to provide the fluid paths illustrated in FIG. 3. A top cover (not shown) fits in a nesting engagement against the container to enclose the components.

Figure 5:
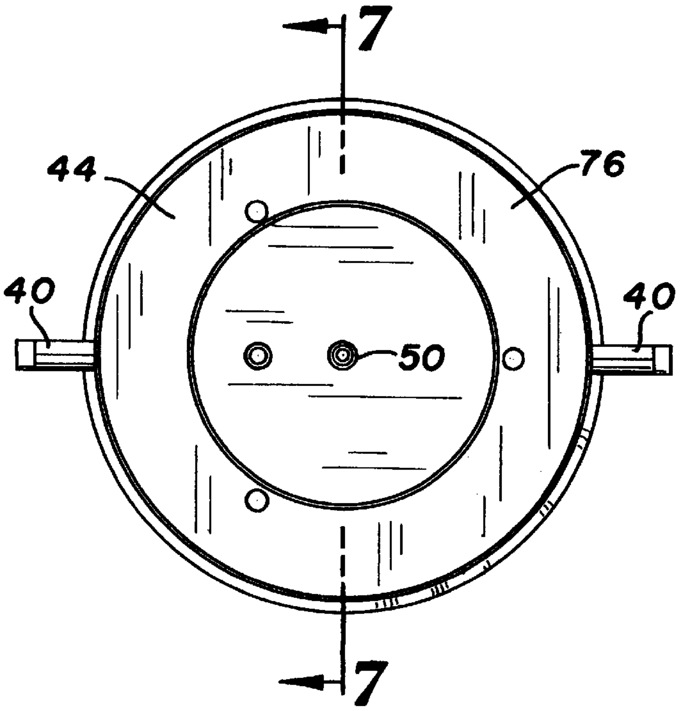
FIG. 5 is a top view of the DMA.
Figure 6:
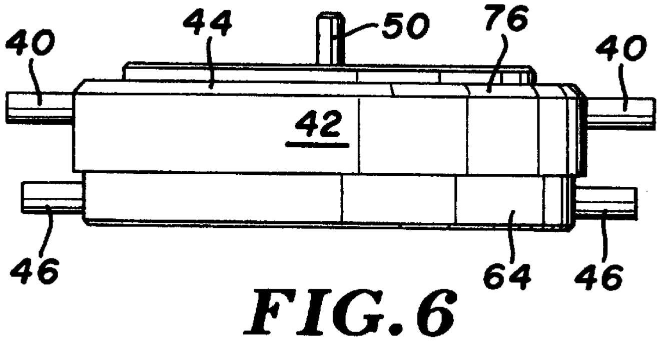
FIG. 6 is a side elevation of the DMA.
Figure 7:
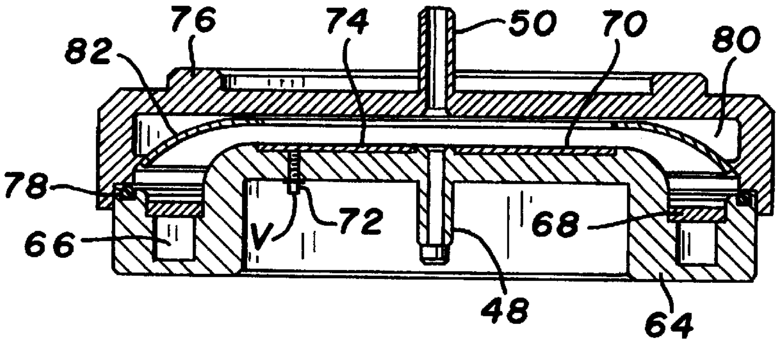
FIG. 7 is a sectional view taken along the line 7—7 in FIG. 5.

FIGS. 5 and 6 show the exterior of radial DMA 42 in greater detail. The interior of the DMA is seen in FIG. 7. The DMA has an annular base 64, preferably formed of an electrically insulative material with strength to provide rigidity, e.g. a polymer with a high modulus of elasticity. Base 64 defines an annular channel 66 for receiving sheath air. A porous plastic ring 68 is supported along the top of channel 66, and acts as a diffuser to provide a laminar air flow upwardly out of the sheath air channel. An electrically conductive plate 70, constructed of stainless steel, is supported within a recess at the top of base 64. Plate 70 is electrically coupled to an electrical power source as indicated schematically at V, for example through a pin or threaded member 72 that extends through a top wall 74 of the base. Exit 48 for the modified aerosol sample is formed along the vertical central axis.

An annular aluminum cover 76 is secured to the base, with a sealing ring 78 provided to ensure that the coupling forms a fluid seal. The cover defines a cylindrical upper chamber 80. Cover 76 further is formed to provide exit 50 for excess air. Like modified sample exit 48, exit 50 is formed along the vertical central axis if the radial DMA. An annular, arcuate divider 82, preferably stainless steel, is disposed between cover 76 and base 64.

The aerosol sample enters chamber 80 at the chamber periphery above divider 82, then flows radially inward toward exits 48 and 50 through a small gap (8–30 mils, more preferably about 15 mils) between divider 82 and the cover. At the same time, sheath air flows upwardly from diffluser ring 68, then radially inward toward the exits for merger with the aerosol sample.

In a manner well known in connection with differential mobility analyzers of all types, particles suspended in the aerosol sample are segregated, in that particles within a particular range of electrical mobility are physically separated from particles in the sample outside of that range. In particular, as the merged sample flow and sheath flow progress radially inward, particles smaller than a certain nominal size, and having a charge opposite that of plate 70, are attracted to the plate and do not reach exits 48 and 50. Meanwhile, larger particles tend to leave the radial DMA through exit port 50. Particles close to the nominal size, and having the opposite charge to that of the plate, are attracted downward yet reach the center of the radial DMA. Consequently, these particles leave the DMA through exit 48 as part of the modified aerosol sample. These latter particles can be considered monodisperse, because they are confined within a considerably narrower size range than the polydisperse elements of the entering aerosol sample.

During testing, the flow rates of the aerosol sample and the sheath air are controlled to maintain the respective flow rates substantially constant, and more particularly to maintain a desired ratio of sheath air flow to sample aerosol flow. For example, the aerosol sample can be provided to the radial DMA at a rate of about 0.7 liters per minute (1 pm) with sheath air flow less than about 3.01 pm. Preferably, sheath flow is kept sufficiently low to provide a ratio of sheath flow/sample flow of at most about 3:1 and at least about 2:1. More preferably, the ratio is about 2.5:1. Typically the sample flow rate is determined at least in part by the particle counter or other measuring device of measuring stage 26 downstream, with the sheath rate adjusted to provide the desired ratio.

The upper end ratio of 3:1 is less than previously preferred sheath/sample flow ratios, typically ranging from 10:1 down to about 4:1. The purpose of the lower flow ratio in DMA 42 is to broaden the transfer function, i.e. the likelihood that a particle entering the DMA will be segregated and removed by the DMA. This has the net effect of increasing the number of segregated particles, while still operating in a region outside of the particles known to penetrate the filter under test.

Another distinguishing feature of system 16 is that the polydisperse elements of the aerosol samples are not subjected to a charging device to be electrically charged as they enter the radial DMA. Rather, the aerosol samples are received in the natural state, with a naturally occurring charge distribution. Although the majority of the elements typically are neutral in the natural state, a substantial proportion of the particles are charged, in most cases resulting in a sufficient count for reasonable statistical accuracy, even though the counted elements might represent only 1–2% of the original polydisburse elements.

Figure 8:
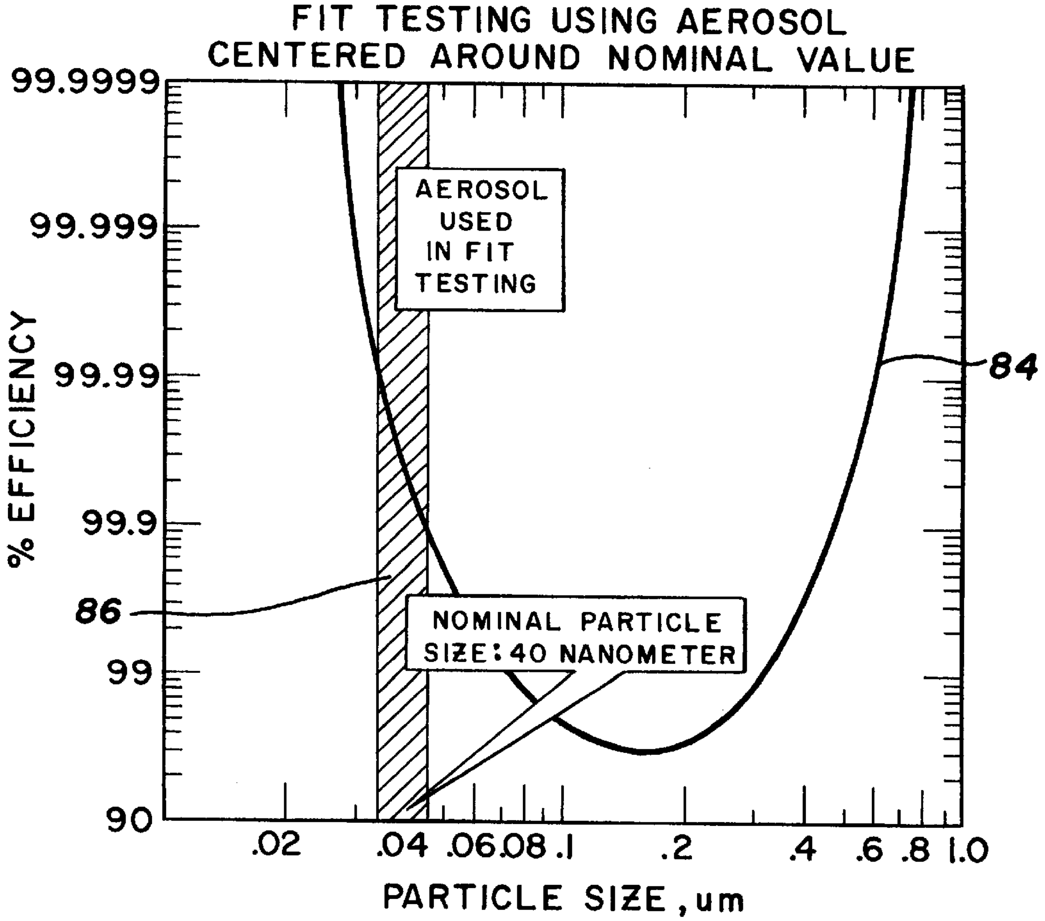
FIG. 8 is a chart illustrating a band of selected aerosol particle sizes, superimposed on a plot of filtration efficiency vs. particle size.

FIG. 8 graphically illustrates segregation of a polydisperse aerosol sample to select particles based on a nominal diameter of 40 mn, with the full bandwidth 86 of selected particles ranging from about 35 nm to about 50 nm. A filtration efficiency plot 84 shows that the filter involved has an efficiency of about 92% at the most penetrating particle size, about 160 nm. However, the filtration efficiency is at least 99.9% throughout selected bandwidth 86, and is considerably higher at the low end of the range.

Figure 9:
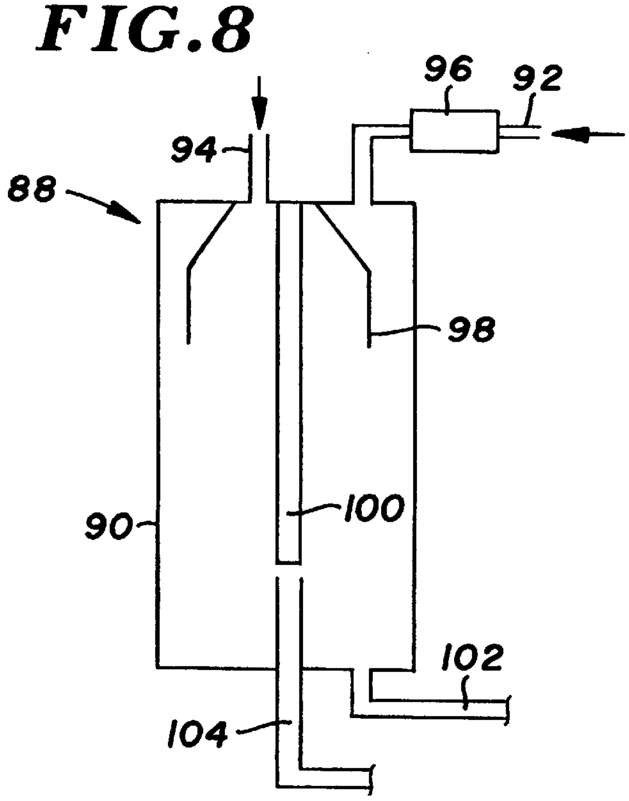
FIG. 9 is a schematic view of a cylindrical differential mobility analyzer adapted for use in lieu of the radial DMA in an alternative embodiment fit-testing system.

According to alternative embodiment systems, several types of instruments are used in lieu of the radial DMA to provide the separating stage. One alternative, shown schematically in FIG. 9, is a differential mobility analyzer (DMA) 88 having an elongate cylindrical configuration. An upright cylindrical housing 90 receives a sample aerosol through an inlet conduit 92, and receives sheath air through an inlet conduit 94 located radically inwardly of the sampling inlet conduit. As before, the aerosol sample inlet conduit alternatively handles the samples taken from inside the respirator mask and proximate but outside the mask. As it flows toward DMA housing 90, the aerosol sample flows through a bipolar charger 96 where the polydisperse elements are charged. The aerosol sample enters the housing radially outwardly of a frusto-conical deflector 98, while the sheath air enters the housing radially inwardly of deflector 98. An axially extended charged rod 100 attracts elements of the opposite charge (typically positive). The outer wall of the housing is grounded.

As the aerosol flows downward, smaller particles that have a greater mobility are attracted to rod 100. Larger particles tend to drift downward to the bottom of housing 90, exiting through an excess air conduit 102. Elements within a narrow size range between the larger and smaller particles are attracted toward rod 100 but are carried past the rod, into a modified aerosol sample conduit 104. Thus, a substantially monodisperse subset of the original polydisperse elements is segregated, in the sense of being physically separated from the rest of the elements, and with air forms a modified aerosol sample provided to the measuring stage downstream.

Given certain ambient conditions and preferences for shorter respirator testing times, a narrow bandwidth of particle or element sizes may not yield a sufficient particle count to provide a desired level of statistical accuracy. In these situations it is desirable to broaden the bandwidth of selected elements. This can be done with a device that segregates all particles smaller than a nominal size.

Figure 11:
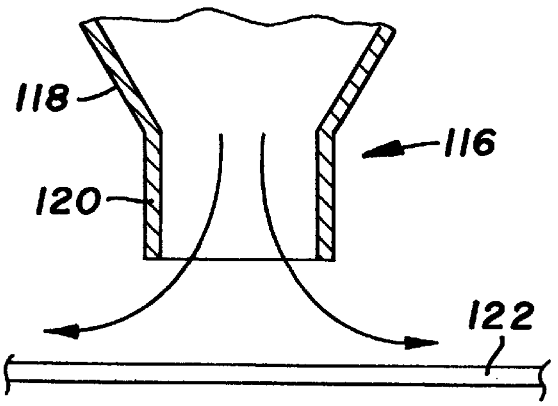
FIG. 11 is a schematic view of an impactor for segregating suspended elements in another alternative embodiment fit-testing system.

For example, according to another embodiment of the invention, particles can be segregated on the basis of inertia rather than electrical mobility. FIG. 11 schematically illustrates an impactor 116 including a converging nozzle 118 that receives the aerosol sample for a downward flow, ajet exit 120 at the bottom of the nozzle, and an impaction plate 122 spaced apart vertically from the jet exit.

As the sample aerosol flows through the impactor downwardly, then radially outwardly as indicated by the arrows, particles of sufficient inertia impact upon the upper surface impaction plate 122. Particles not impacting the plate, i.e. the smaller particles with an inertia at or below a nominal level, proceed to a measurement stage as part of a modified aerosol sample. The nominal level of inertia is influenced by a variety of factors, including flow volocity, dimensions of the nozzle and jet exit, and spacing between the jet exit and the impaction plate.

Figure 10:
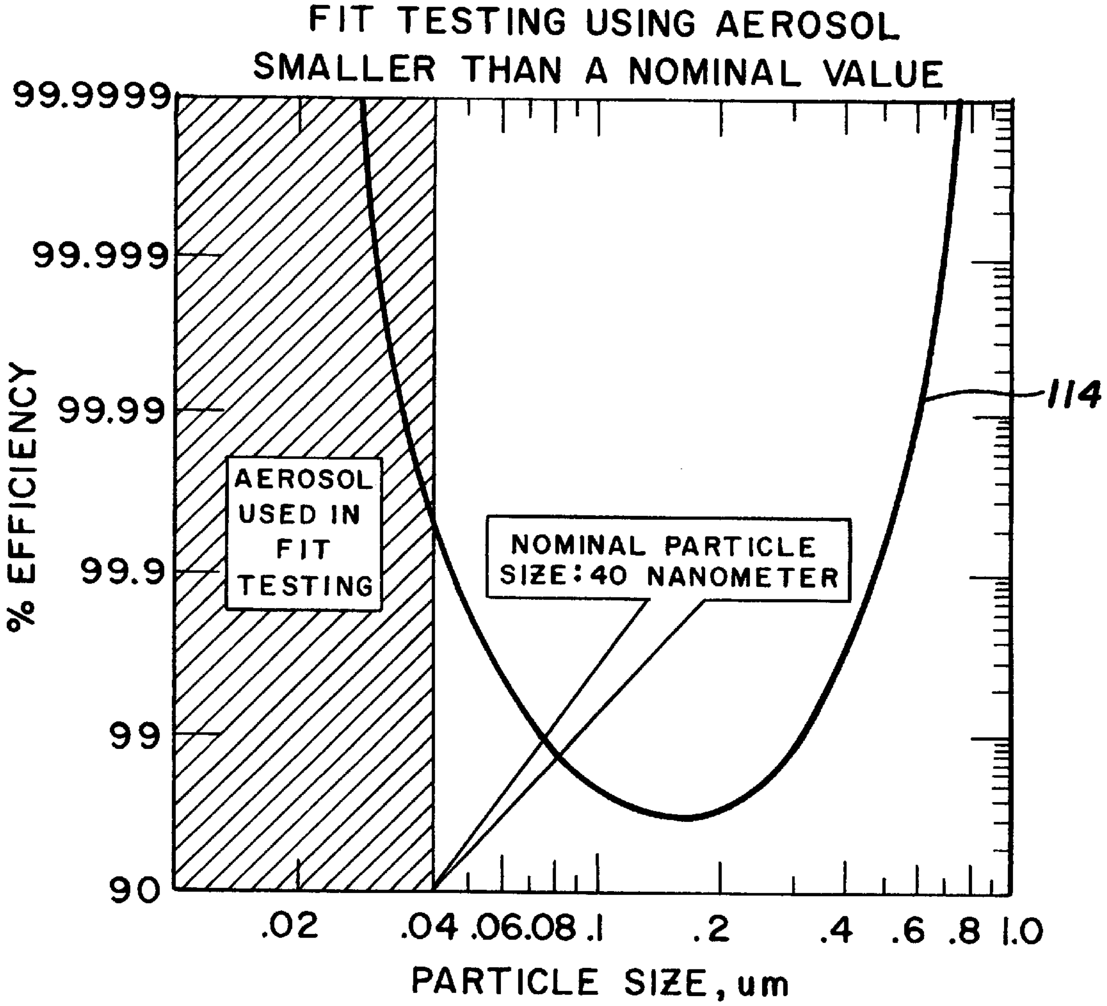
FIG. 10 is a chart superimposing a broad range of particle sizes superimposed on a plot of filtration efficiency vs. particle size.

Consequently, the elements in the modified aerosol sample remain somewhat polydisperse. This result is seen in FIG. 10, where a filtration efficiency plot 114 indicates maximum penetration at a particle size of about 160 mn. Particles or other elements are segregated, based on a nominal diameter of 40 nm, with the shaded area on the graph indicting that all elements having a 40 nm diameter or smaller are retained in the modified aerosol sample. The minimum filtration efficiency within this range, about 99.92%, occurs at the 40 nm size.

Thus, a broader bandwidth of particles is selected for concentration measurements. When broadening the bandwidth in this fashion, it is important to select a particle measuring instrument that is sensitive to smaller diameter particles, e.g., a condensation particle counter.

Other devices suitable for segregating particles by inertia include virtual impactors, cyclones, horizontal elutriators, and centrifugal separators.

As an alternative or additional step to increase the number of elements in the measured samples, it may be desirable to supplement the naturally occurring aerosol with a generated polydisperse aerosol. This can be done using a simple self-contained compressor and atomizer as a polydisperse aerosol generator, utilizing a 2% salt solution. This generator produces an additional 3,000 to 5,000 particles/cc which combine with the naturally occurring ambient aerosol near the mask. The additional particles increase the number of elements segregated from the sampled aerosol, and increase the statistical validity of the measurements.

Regardless of the type of device or instrument used for particle/element segregation, the operating principle is the same: namely, to segregate a portion of a polydisperse aerosol to produce a modified aerosol in which virtually all of the suspended particles are within a range known to have an acceptably low penetration rate for the filter under test. Because any leakage generally is independent of the particle size involved, the fit factors are no less reliable for the fact that they are based on modified aerosol samples with more limited bandwidths of particle sizes.

Returning to FIG. 2, the output of separating stage 24 is provided to concentration measuring stage 26. The output includes, alternatively, a first modified aerosol sample based on the original sample taken from within respirator mask 33, and a second modified sample reflecting the ambient sample taken near the respirator.

Figure 12:
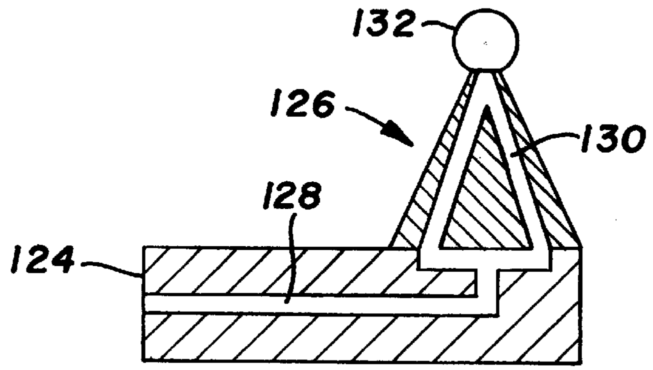
FIG. 12 is a schematic view of a condensation particle counter for generating element concentration values in the test system.

In the presently preferred version of system 16, the modified aerosol samples are provided as the alternative outputs of radial DMA 42, to an inlet 124 of a condensation particle counter 126 (FIG. 12), which can be similar to the device described in U.S. Pat. No. 4,790,650 (Keady). Briefly, the modified aerosol sample entering inlet 124 proceeds through a saturation zone 128, where butyl alcohol or another volatile liquid is continually evaporated into the gas stream. The gas stream, substantially saturated, proceeds into a condensation zone 130, where the aerosol is cooled sufficiently to cause the volatile liquid to condense onto the suspended particles, in effect "growing" each particle to a larger effective size for easier detection. The enlarged particles proceed to an optical detection zone 132, where individual particles pass through and momentarily interrupt a laser beam, thus to generate a particle recognition signal and add to an accumulated particle count. For an aerosol sample of a given volume, the accumulated particle count is a concentration value that indicates the concentration of particles suspended in the aerosol. The output of condensation particle counter 126 includes first and second concentration values, associated with the first and second modified aerosol samples, respectively.

When the modified aerosol sample consists of or has a substantial proportion of particles less than 1 micron in diameter, condensation particle counter 126 is the preferred instrument at the concentration measuring stage. An electrometer is a suitable alternative under these circumstances. Conversely, other aerosol separation devices, e.g., virtual impactors, generate size-selected aerosols with suspended particles larger than 0.5 microns in diameter. In such cases, an optical particle counter or photometer may be used to generate concentration values. Thus, measurement of scattered light intensities can be used in lieu of particle counting.

Returning again to FIG. 2, the respective concentration values are provided to processing stage 28, where they are compared to generate a ratio of the ambient concentration value to the mask concentration value, i.e. the fit factor.

Figure 13:
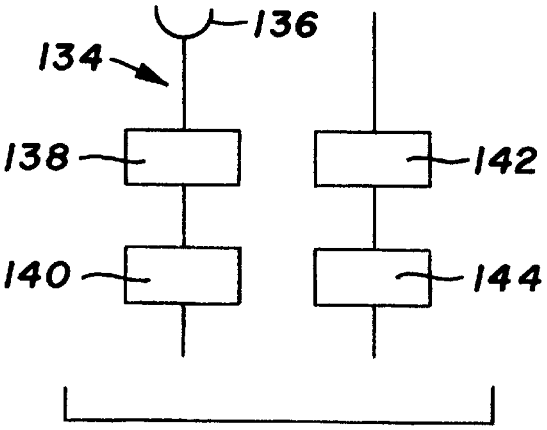
FIG. 13 illustrates a further alternative embodiment respirator testing system employing individual separation and concentration-determining stages.

FIG. 13 illustrates an alternative embodiment system 134 with independent paths for simultaneously generating ambient and mask concentration values. In particular, a polydisperse aerosol sample from inside a respirator 136 is provided to a radial DMA or other separator 138, which in turn provides a modified aerosol sample to a condensation particle counter or other measuring instrument 140, which provides as its output a concentration value reflecting conditions inside the respirator mask. Simultaneously, an ambient sample is provided to a separator 142, which provides a modified aerosol sample to a measuring instrument 144, the output of which is a concentration value indicating ambient conditions near the respirator.

System 134 eliminates the need to provide alternative samples and generate alternative concentration values, thus reducing the time necessary for testing the respirator. However, the use of different separating devices and different measurement devices introduces several additional sources of potential error in determining the fit factor.

Figure 14:
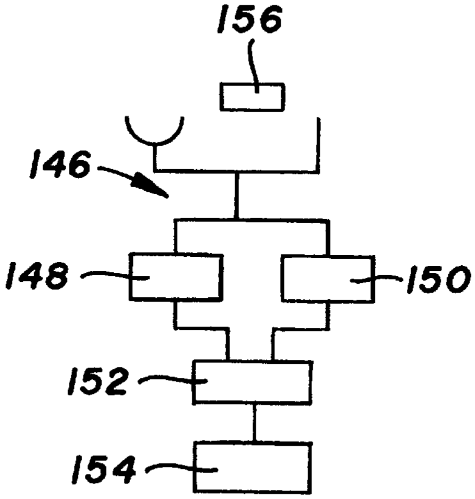
FIG. 14 illustrates another respirator testing system employing alternative particle separation stages in combination with a single particle counting stage.

FIG. 14 illustrates a further alternative embodiment system 146 in which respective ambient and respirator aerosol samples are provided, alternatively, either to a radial DMA 148 or an impactor 150 at the separating stage, and then from the separating stage to a condensation particle counter 152 which provides the respective concentration values to a processor 154. The primary advantage of system 146 is flexibility, in that the segregation of suspended particles can be based on a narrow bandwidth of sizes using the DMA, or based on a larger bandwidth by switching to impactor 150, when DMA 148 is found to yield an insufficient number of suspended particles for a desired level of statistical accuracy. Alternatively (or in addition), an aerosol generator 156 can provide a supplemental aerosol for measurement in combination with the ambient aerosol.

Thus, in accordance with the present invention, a respirator can be fit-tested based on sampling polydisperse aerosols under ambient conditions, even when the respirator filter has an unacceptably high penetration rate for certain sizes of particles. Suspended particles in the aerosol samples are segregated, to retain in modified aerosol samples only particles for which the tested filter has a high filtration efficiency. The particles having high tendencies to penetrate the filter are physically removed, and thus are prevented from contaminating results intended to reflect leakage alone. There is no need for devices that generate prescribed artificial atmospheres, and no need for enclosures to confine individuals within such atmospheres during testing. In addition to considerably reducing the cost of fit-testing, the system affords an individual more freedom of movement to perform tasks and movements anticipated under normal working conditions.

What is claimed is:

1. A process for the quantitative fit-testing of a respirator, including:

fitting a respirator having a filter to an individual, so that the respirator in cooperation with the individual's face forms an internal breathing chamber;

collecting first and second aerosol samples from outside of the respirator and from the breathing chamber, respectively;

segregating elements suspended in the first and second aerosol samples according to a predetermined element characteristic to select only elements that exceed a fractional filtration efficiency threshold with respect to the filter, while providing the aerosol samples as first and second aerosol sample flows at substantially constant sample flow rates, to provide first and second modified samples corresponding to the first and second aerosol samples, respectively; and generating first and second aerosol concentration values indicating concentrations of the selected elements in the first modified sample and in the second modified sample, respectively.

2. The process of claim 1 wherein:

said segregating of the elements further comprises providing a sheath air flow at a substantially constant sheath air flow rate in combination with each of the sample flows, at a ratio of sheath flow/sample flow in the range of about 2:1 to about 3:1.

3. The process of claim 1 further including:

comparing the first and second concentration values to indicate a degree of resistance to leakage into the enclosure.

4. The process of claim 1 wherein:

said predetermined element characteristic is size, and said segregating the elements suspended in the first and second aerosol samples comprises a step selected from the group of steps consisting of: selecting elements with diameters within a predetermined range of diameters; and selecting elements having diameters below a predetermined diameter.

5. The process of claim 1 wherein:

said predetermined element characteristic is selected from the group of characteristics consisting of: electrical mobility; and inertia.

6. The process of claim 1 wherein:

the generating of the first and second aerosol concentration values comprises counting individual elements.

7. The process of claim 1 wherein:

the generating of the first and second concentration values comprises measuring scattered light intensities.

8. The process of claim 1 further including:

after collecting the first and second aerosol samples, electrically charging the elements suspended in the first and second aerosol samples.

9. A process for quantitative fit-testing of a respirator, including:

fitting a respirator having a filter to an individual, so that the respirator in cooperation with the individual's face forms an internal breathing chamber;

collecting first and second aerosol samples from outside of the respirator and from the breathing chamber, respectively;

electrically charging the elements suspended in the first and second aerosol samples;

after electrically charging the elements, segregating the elements suspended in the first and second aerosol samples according to a predetermined element characteristic to select only elements that exceed a fractional filtration efficiency threshold with respect to the filter, to provide first and second modified samples corresponding to the first and second aerosol samples, respectively; and generating first and second aerosol concentration values indicating concentrations of the selected elements in the first modified sample and in the second modified sample, respectively.

10. The process of claim 9 wherein:

said predetermined element characteristic is size, and said segregating the elements suspended in the first and second aerosol samples comprises a step selected from the group of steps consisting of: selecting elements with diameters within a predetermined range of diameters; and selecting elements having diameters below a predetermined diameter.

11. The process of claim 9 wherein:

the generating of the first and second aerosol concentration values comprises counting individual elements.

12. The process of claim 9 wherein:

the generating of the first and second concentration values comprises measuring scattered light intensities.

13. The process of claim 9 further including:

generating a ratio of the first aerosol concentration value to the second aerosol concentration value, and indicating a rejection of the filtration device due to excessive leakage if the ratio is less than a predetermined minimum.

14. The process of claim 9 wherein:

said segregating the elements suspended in the first and second aerosol samples comprises providing the aerosol samples respectively as first and second aerosol sample flows at substantially constant sample flow rates.

15. A system for the quantitative fit-testing of a respirator, including:

a means for collecting a first aerosol sample from outside of a respirator having a filter, and for collecting a second aerosol sample from a breathing chamber formed inside of a respirator when worn by an individual;

an aerosol separating device for receiving the first and second aerosol samples as respective first and second aerosol flows each having a substantially constant sample flow rate, for separating from each of the aerosol samples a portion of polydisperse elements suspended therein according to a predetermined aerosol characteristic to exclude at least those elements that exceed a penetration threshold chosen with respect to the filter, to provide first and second modified samples corresponding to the first and second aerosol samples, respectively; and an aerosol concentration measuring device, coupled with respect to the separating device to receive the first and second modified samples individually, for generating first and second concentration values indicating the concentration of the elements in the first modified sample and in the second modified sample, respectively.

16. The system of claim 15 wherein:

the aerosol separating device includes means for providing sheath air at a substantially constant sheath flow rate, and a means for combining the sheath air flow alternatively with each of the sample flows, at a ratio of sheath flow/sample flow in the range of about 2:1 to about 3:1.

17. The system of claim 15 wherein:

the means for collecting a first and second aerosol samples includes a first conduit coupled to the aerosol separating device and open to the atmosphere outside of and adjacent the respirator and a means for drawing the aerosol through the first conduit toward the aerosol separating device; and a second conduit coupled to the aerosol separating device and open to the breathing chamber, and a means for drawing the aerosol through the second conduit toward the aerosol separating device.

18. The system of claim 15 wherein:

the aerosol separating device is adapted to distinguish among individual elements based on electrical mobility.

19. The system of claim 18 further including:

a means for electrically charging the elements suspended in the first and second aerosol samples as the first and second aerosol flows move toward the aerosol separating device.

20. The system of claim 18 wherein:

the aerosol separating device comprises a differential mobility analyzer.

21. The system of claim 15 wherein:

the aerosol separating device distinguishes among individual elements based on their inertia.

22. The system of claim 15 wherein:

the aerosol concentration measuring device is adapted to accumulate counts of individual elements.

23. The system of claim 15 further including:

a charger for applying an electrical charge to the polydisperse elements suspended in the first and second aerosol samples as the aerosol samples approach the aerosol separating device.

24. A system for the quantitative fit-testing of a respirator, including:

a means for collecting a first aerosol sample from outside of a respirator having a filter, and for collecting a second aerosol sample from a breathing chamber formed inside of a respirator when worn by an individual;

an aerosol separating device for receiving the first and second aerosol samples individually, for separating from each of the aerosol samples a portion of the polydisperse elements suspended therein according to a predetermined aerosol characteristic to exclude at least those elements that exceed a penetration threshold chosen with respect to the filter, to provide first and second modified samples corresponding to the first and second aerosol samples, respectively;

a charger for applying an electrical charge to the polydisperse elements suspended in the aerosol sample as the aerosol sample approaches the aerosol separating device; and an aerosol concentration measuring device, coupled with respect to the separating device to receive the first and second modified samples individually, for generating first and second concentration values indicating the concentration of the elements in the first modified sample and in the second modified sample, respectively.

25. The system of claim 24 wherein:

the means for collecting a first and second aerosol samples includes a first conduit coupled to the aerosol separating device and open to the atmosphere outside of and adjacent the respirator and a means for drawing the aerosol through the first conduit toward the aerosol separating device; and a second conduit coupled to the aerosol separating device and open to the breathing chamber and a means for drawing the aerosol through the second conduit toward the aerosol separating device.

26. The system of claim 24 wherein:

the aerosol separating device is adapted to distinguish among individual elements based on electrical mobility.

27. The system of claim 24 wherein:

the aerosol separating device comprises a differential mobility analyzer.

28. The system of claim 24 wherein:

the aerosol concentration measuring device is adapted to accumulate counts of individual elements.

29. The system of claim 24 wherein:

said aerosol separating device receives the first and second aerosol samples as respective first and second aerosol flows each having a substantially constant sample flow rate.

30. A system for the quantitative fit-testing of a respirator, including:

a means for collecting a first aerosol sample from outside of a respirator having a filter, and for collecting a second aerosol sample from a breathing chamber formed inside of a respirator when worn by an individual;

an aerosol separating device for receiving the first and second aerosol samples individually, for separating from each of the aerosol samples a portion of the polydisperse elements suspended therein according to a predetermined aerosol characteristic to exclude at least those elements that exceed a penetration threshold chosen with respect to the filter, to provide first and second modified samples corresponding to the first and second aerosol samples, respectively; and an aerosol concentration measuring device, coupled with respect to the separating device to receive the first and second modified samples individually, for generating first and second concentration values indicating the concentration of the elements in the first modified sample and in the second modified sample, respectively;

wherein the means for collecting the first and second aerosol samples includes a first conduit coupled to the aerosol separating device and open to the atmosphere outside of and adjacent the respirator and a means for drawing the first aerosol through the first conduit toward the aerosol separating device, and a second conduit coupled to the aerosol separating device and open to the breathing chamber and a means for drawing the second aerosol through the second conduit toward the aerosol separating device.

31. The system of claim 30 further including:

an aerosol generator for providing a supplemental aerosol outside of and adjacent the respirator.

32. The system of claim 30 wherein:

the aerosol separating device is adapted to distinguish among individual elements based on electrical mobility.

33. The system of claim 32 wherein:

the aerosol separating device comprises a differential mobility analyzer.

34. The system of claim 32 further including:

a means for electrically charging the elements suspended in the first and second aerosol samples as the first mid second aerosol flows move toward the aerosol separating device.

35. The system of claim 30 wherein:

the aerosol separating device distinguishes among individual elements based on their inertia.

36. The system of claim 35 wherein:

the aerosol separating device includes a device selected from the set of devices consisting of: an impactor, a virtual impactor, a cyclone, a horizontal elutriator, and a centrifugal separator.

37. The system of claim 30 wherein:

the aerosol concentration measuring device is adapted to accumulate counts of individual elements.

38. The system of claim 37 wherein:

the aerosol concentration measuring device is selected from the group of devices consisting of: a condensation particle counter, an electrometer, a photometer, and an optical particle counter.

39. The system of claim 30 wherein:

the aerosol separating device receives the first and second aerosol samples as respective first and second aerosol flows each having a substantially constant sample flow rate.

40. The system of claim 30 further including:

a charger for applying an electrical charge to the polydisperse elements suspended in the first and second aerosol samples as the aerosol samples approach the aerosol separating device.

* * * * *